US009802005B2

(12) United States Patent
Olson

(10) Patent No.: US 9,802,005 B2
(45) Date of Patent: Oct. 31, 2017

(54) MEDICAMENT DELIVERY DEVICE

(71) Applicant: Carebay Europe Ltd, Swatar (MT)

(72) Inventor: Stephan Olson, Danderyd (SE)

(73) Assignee: Carebay Europe Ltd, Sliema (MT)

( * ) Notice: Subject to any disclaimer, the term of this patent is extended or adjusted under 35 U.S.C. 154(b) by 42 days.

(21) Appl. No.: 14/432,266

(22) PCT Filed: Sep. 25, 2013

(86) PCT No.: PCT/EP2013/069995
§ 371 (c)(1),
(2) Date: Mar. 30, 2015

(87) PCT Pub. No.: WO2014/053378
PCT Pub. Date: Apr. 10, 2014

(65) Prior Publication Data
US 2015/0273160 A1    Oct. 1, 2015

Related U.S. Application Data

(60) Provisional application No. 61/709,183, filed on Oct. 3, 2012.

(30) Foreign Application Priority Data

Oct. 3, 2012    (SE) ........................ 1251113

(51) Int. Cl.
*A61M 5/20*    (2006.01)
*A61M 5/32*    (2006.01)
(Continued)

(52) U.S. Cl.
CPC ........ *A61M 5/3257* (2013.01); *A61M 5/2033* (2013.01); *A61M 5/3134* (2013.01);
(Continued)

(58) Field of Classification Search
CPC .... A61M 2005/2013; A61M 2005/206; A61M 2005/208; A61M 2005/3267; A61M 5/3257
See application file for complete search history.

(56) References Cited

U.S. PATENT DOCUMENTS 5,085,641 A * 2/1992 Sarnoff ............... A61M 5/2033
604/134
5,820,602 A * 10/1998 Kovelman ............ A61M 5/172
604/156
(Continued)

FOREIGN PATENT DOCUMENTS

EP    2399627 A1    12/2011
EP    2596826 A1    5/2013
(Continued)

OTHER PUBLICATIONS

EPO, Int'l Search Report in PCT/EP2013/069995, dated Jun. 2, 2014.
EPO, Written Opinion in PCT/EP2013/069995, dated Jun. 2, 2014.

*Primary Examiner* — Aarti B Berdickevsky
(74) *Attorney, Agent, or Firm* — Piedmont Intellectual Property

(57) ABSTRACT

An injection device with distal and proximal ends includes a housing, a needle-protecting sleeve that is longitudinally movable relative to the housing, a container holder that is longitudinally movable relative to the housing toward the proximal end from a non-delivery position to a delivery position, and a needle-protecting sleeve spring that is operatively coupled between the needle-protecting sleeve and the container holder such that the sleeve is longitudinally movable toward the distal end from an initial position to an activating position and toward the proximal end from the activating position to an end position. The sleeve spring is strained by a first amount when the sleeve moves from its (Continued)

Figure 1:
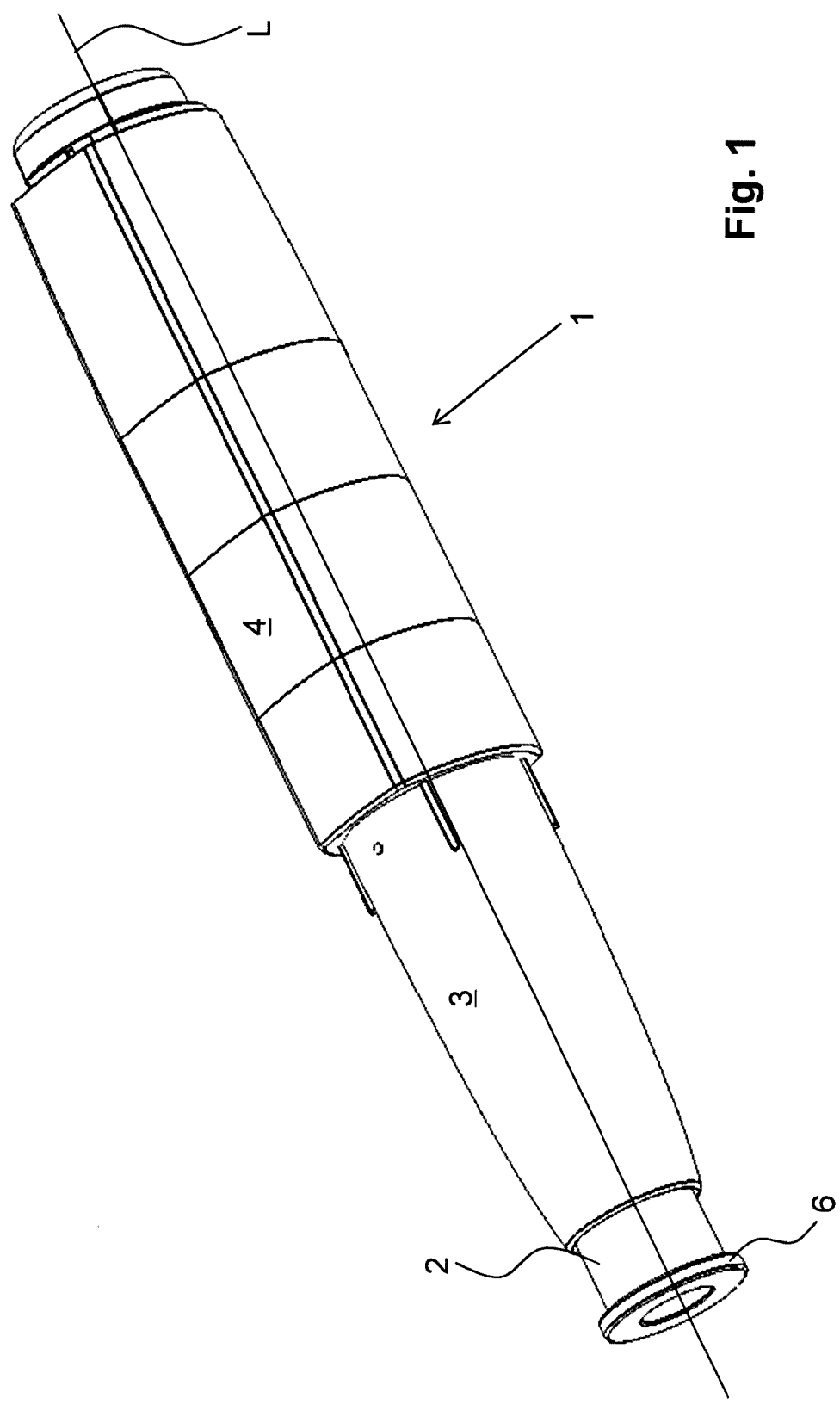

initial position to its activating position, and by a second amount when the container holder moves from its non-delivery position to its delivery position.

20 Claims, 10 Drawing Sheets

(51) Int. Cl.
    *A61M 5/31*     (2006.01)
    *A61M 5/28*     (2006.01)

(52) U.S. Cl.
    CPC ............... *A61M 5/326* (2013.01); *A61M 5/28* (2013.01); *A61M 5/3272* (2013.01); *A61M 2005/206* (2013.01); *A61M 2005/208* (2013.01); *A61M 2005/2013* (2013.01); *A61M 2005/2073* (2013.01); *A61M 2005/3267* (2013.01)

(56) References Cited

U.S. PATENT DOCUMENTS

| | | | |
|---|---|---|---|
| 2003/0105430 A1 | 6/2003 | Lavi et al. | |
| 2008/0051715 A1* | 2/2008 | Young | A61M 5/2033 604/135 |
| 2009/0270804 A1 | 10/2009 | Mesa et al. | |
| 2012/0101475 A1* | 4/2012 | Wilmot | A61M 5/2033 604/506 |
| 2013/0112521 A1* | 5/2013 | Ekman | A61M 5/20 192/69.8 |
| 2013/0131602 A1* | 5/2013 | Kemp | A61M 5/2033 604/197 |
| 2013/0296795 A1* | 11/2013 | Ekman | A61M 5/2033 604/197 |

FOREIGN PATENT DOCUMENTS

| | | |
|---|---|---|
| WO | 02/47746 A1 | 6/2002 |
| WO | 2009/040602 A1 | 4/2009 |
| WO | 2013/032389 A1 | 3/2013 |

* cited by examiner

# MEDICAMENT DELIVERY DEVICE

BACKGROUND

The invention relates to medicament delivery devices. More particularly, it relates to an injection device, such as an auto-injector, for injecting a fluid medicament, wherein after the medicament has been delivered, a needle protecting sleeve associated with the injection device is moved or slid to cover the injection needle.

Moving or sliding a needle protecting sleeve in a proximal direction, from a distal position in which the needle is exposed, by using a spring, such that the needle is covered and protected against being accessed, is known from WO2002047746A1. The spring which forces the needle protecting sleeve to move or slide over the injection needle is pre-tensioned by an amount. When the needle protecting sleeve is moved or slid beyond the injection needle, the spring force decreases according to the rules of Hooke's Law. Thus, the spring has to be pre-tensioned such that the needle protecting sleeve can reliably assume an end position in which it fully covers the injection needle. However, a problem is that having a device with pre-tensioned springs acting on plastic components in storage for long periods of time may deform the plastic components. Also, having a device that is triggered or partially triggered by shifting the needle protecting sleeve from a proximal position into a distal position the spring is further tensioned by a further amount. A further problem is to obtain a balance of forces since it is desirable that the force needed to shift the needle protecting sleeve in the distal direction is low, to make it easier for the user to handle the device and on the other hand, an increased spring force is desirable for shifting the needle protecting sleeve in the proximal direction from the distal position.

SUMMARY

In order to overcome one or several of the above-mentioned problems, an injection device according to claim 1 is provided.

In the present application, when the term "distal" is used, this refers to the direction pointing away from the dose delivery site. When the term "distal part/end" is used, this refers to the part/end of the delivery device, or the parts/ends of the members thereof, which is/are located furthest away from the dose delivery site. Correspondingly, when the term "proximal" is used, this refers to the direction pointing to the dose delivery site. When the term "proximal part/end" is used, this refers to the part/end of the delivery device, or the parts/ends of the members thereof, which is/are located closest to the dose delivery site.

It is therefore an object of the present invention to provide an injection device in which the needle protecting sleeve spring that forces the needle protecting sleeve in a proximal direction, from an activation position in which the needle is exposed, can be pre-tensioned during the activation and during the delivery process with an amount that allows the needle protecting sleeve to reliably assume an end position in which it covers the injection needle.

In one embodiment, the present invention comprises an injection device having a distal and a proximal end comprising a housing, a needle protecting sleeve longitudinally movable relative to the housing, a container holder longitudinally movable relative to the housing towards the proximal end of the device, from a non-delivery position into a delivery position, a needle protecting sleeve spring operably coupled between the needle protecting sleeve and the container holder such that the needle protecting sleeve can be longitudinally moved towards the distal end of the device from an initial position into an activating position and towards the proximal end of the device from the activating position into an end position, wherein the needle protecting sleeve spring is strained by a first amount when the needle protecting sleeve moves from its initial position to the activating position, and by a second amount when the container holder moves from the non-delivery position to the delivery position. More particularly, the needle protecting sleeve can be longitudinally moved towards the proximal end of the device from the activating position into an end position by the needle protecting sleeve spring. Further, the second amount of straining may be larger than the first amount of straining.

In some preferred embodiments, the needle protecting sleeve spring is operably coupled between the needle protecting sleeve and a proximal end of the container holder.

In some embodiments, the housing can comprise one part or multiple parts, for example it may comprise a distal housing part and a proximal housing part which is latched, axially fixed, to the distal housing part. A multiple part housing offers advantages when assembling the injection device.

In all embodiments, the injection device comprises a medicament container having a needle and a stopper/piston, said medicament container being arranged within the container holder.

In all embodiments, the injection device comprises a drive mechanism by which the container holder together with the medicament container can be longitudinally moved relative to the housing towards the proximal end of the device from the non-delivery position into the delivery position when the needle protecting sleeve is in the activating position, such that in the delivery position, the needle arranged on the medicament container protrudes beyond the proximal end of the injection device.

In some embodiments, the injection device also comprises an activating member which is embodied as the needle protecting sleeve. In some preferred embodiments, the needle protecting sleeve can be shifted distally from an initial position into an activating position and proximally from the activating position into an end position. In the initial position, the needle protecting sleeve protrudes proximally a predetermined distance beyond the proximal end of the housing. In the activating position, the needle protecting sleeve also protrudes proximally beyond the proximal end of the housing by a lesser distance than in the initial position or the proximal edge of the needle protecting sleeve is parallel i.e. flush with the proximal edge of the housing e.g. the proximal end of the housing comes into contact with the delivery site. In the end position, the needle protecting sleeve protrudes proximally beyond the proximal end of the housing by a larger distance than in the initial position.

In some preferred embodiments, when the needle protecting sleeve is in the end position, it protrudes beyond the proximal end of the injection needle and is locked to prevent accidental needle sticks. The needle protecting sleeve also protrudes beyond the proximal end of the injection needle in the initial position. However, the needle protecting sleeve is not locked. When the needle protecting sleeve is situated in the activating position, the injection needle may be advanced far enough beyond the proximal end of the needle protecting sleeve such that the needle length which protrudes beyond said proximal end corresponds to the injection depth. The needle protecting sleeve is designed to be placed onto a delivery site/injection location provided on the patient. When the placed injection device is pressed onto the injection location, the needle protecting sleeve is shifted from the initial position into the activating position, i.e. into the distal position in this case; this can be thought of as activating the needle protecting sleeve. The needle protecting sleeve is designed to activate the drive mechanism for penetrating the injection needle and delivering the product, i.e. for example to effect a mechanical switch.

In some preferred embodiments, the drive mechanism comprises at least one spring for moving the container holder together with the medicament container towards the proximal end of the device and for expelling the medicament, and wherein the needle protecting sleeve spring, which is operably coupled between the needle protecting sleeve and the container holder, can be tensioned to the second amount.

In some embodiments, the drive mechanism is configured to hold the at least one spring in a pre-tensioned state.

In some preferred embodiments, in its end position, the needle protecting sleeve is latched, axially fixed, relative to the housing. The latching reduces the danger of injury, since the needle protecting sleeve is prevented from being inadvertently retracted, which would cause the injection needle to protrude.

In a preferred embodiment, a further triggering element can be provided which releases a blocking/holding connection to the drive mechanism, which prevents the drive mechanism to be released, such that a penetration and delivery movement can be performed. Thus, the needle protecting sleeve has to be activated in addition to the triggering element to enable the blocking/holding connection to be released.

DETAILED DESCRIPTION OF THE DRAWINGS

Figure 2:
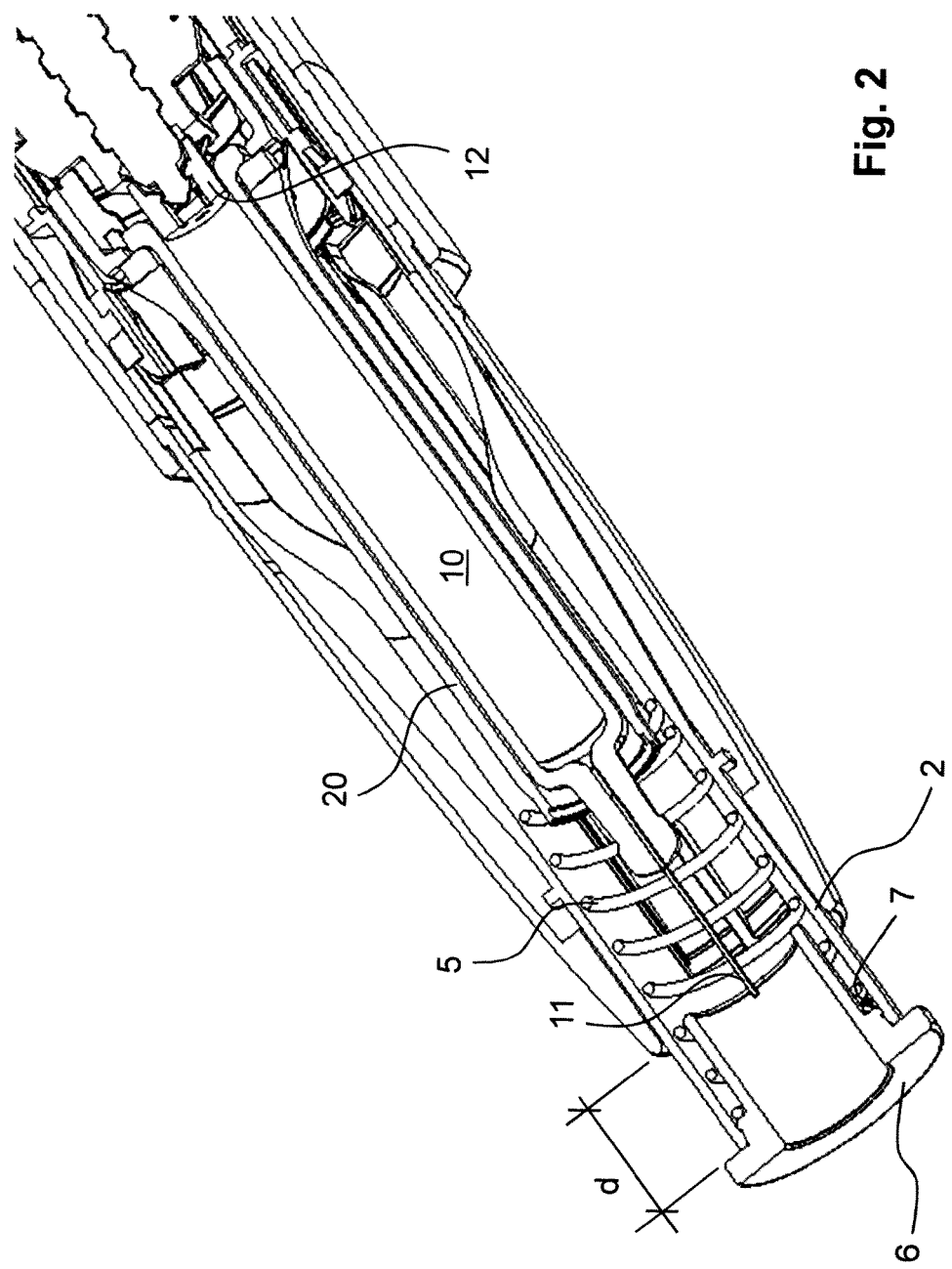
Figure 3:
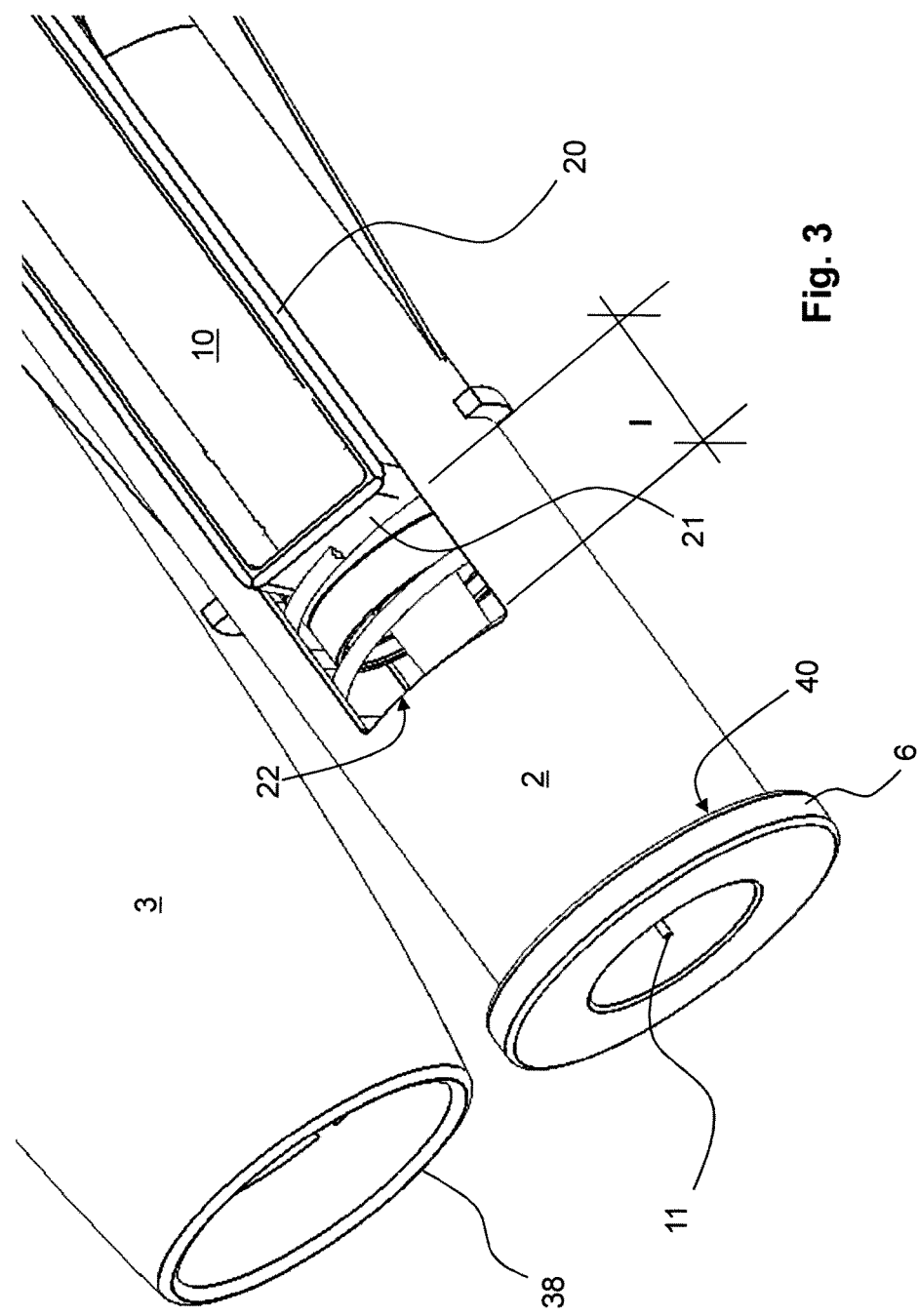
Figure 4:
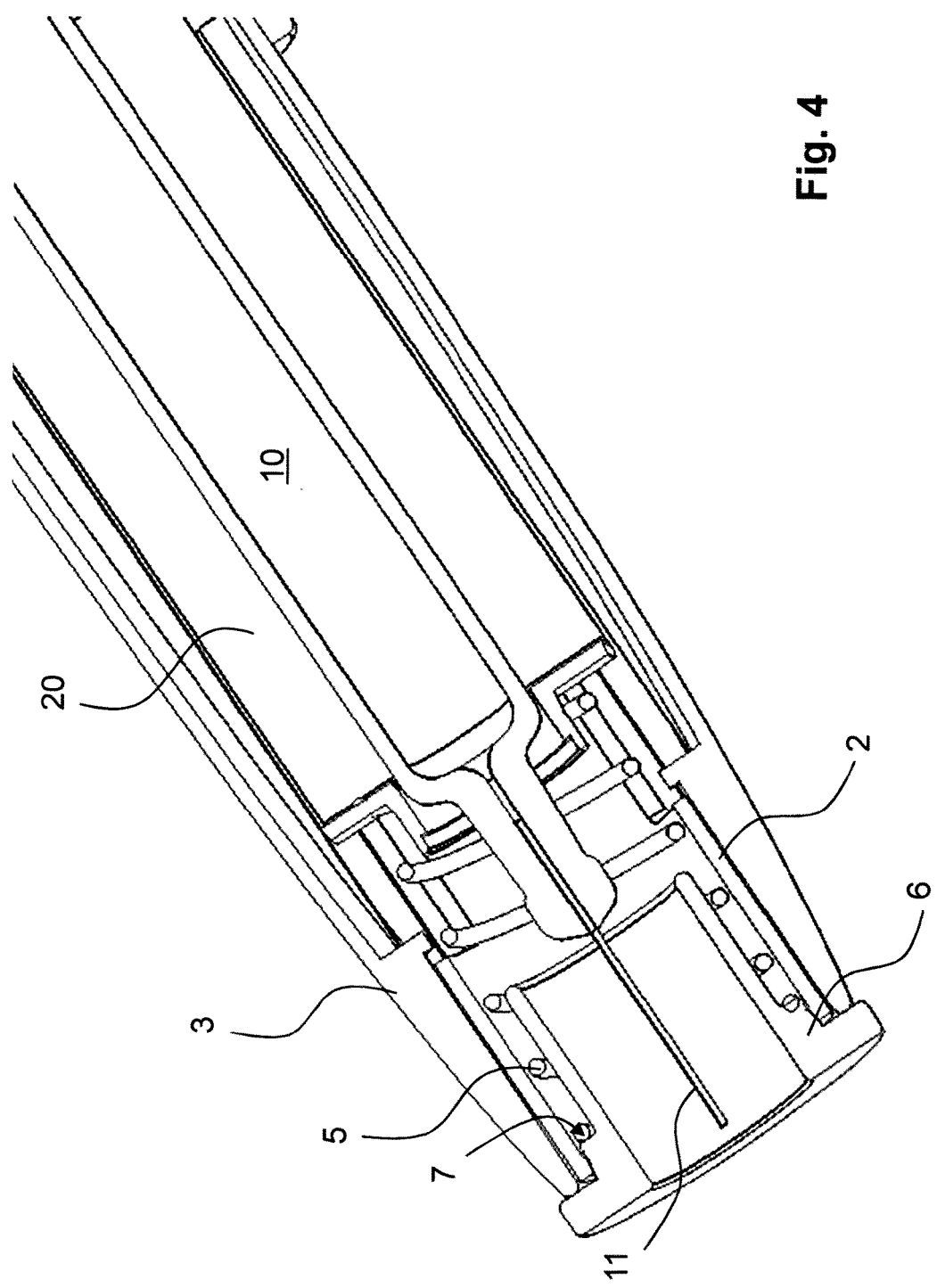
Figure 5:
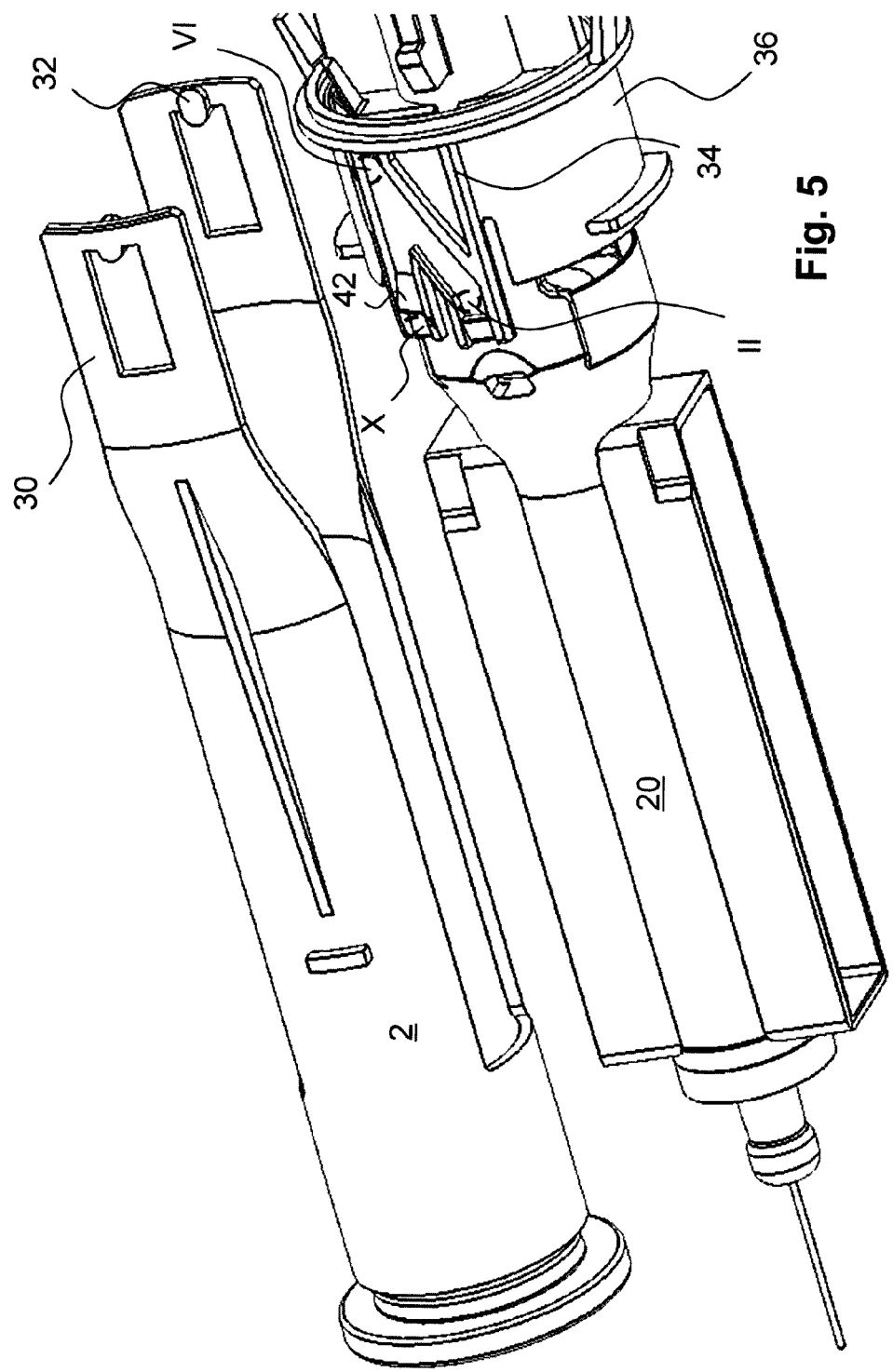
Figure 6:
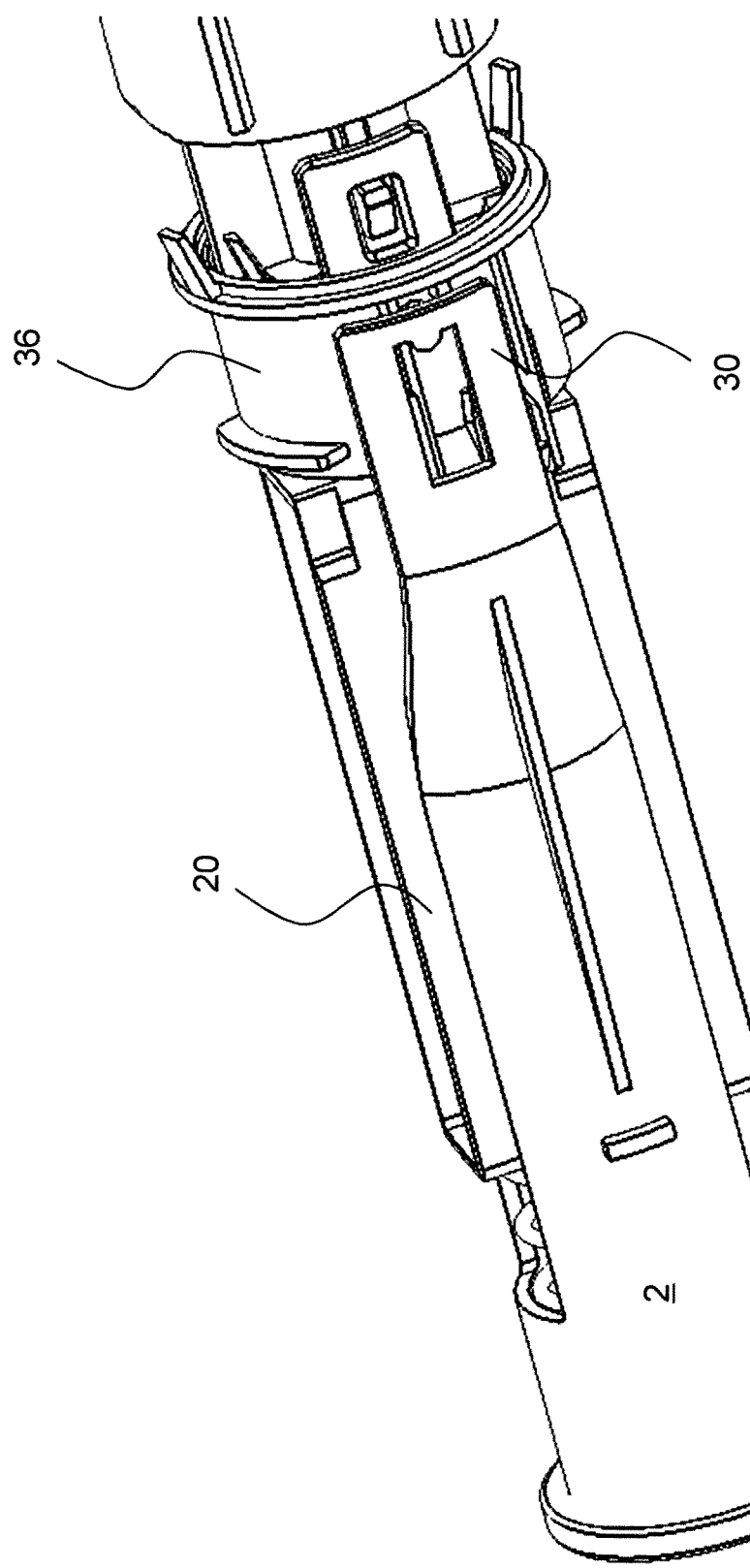

In the detailed description of the invention, reference will be made to the accompanying drawings, of which FIG. 1 is a perspective view of a medicament delivery device according to an embodiment of the invention, FIG. 2 is cross-sectional view of a proximal part of the device of FIG. 1 in an initial state, FIG. 3 is a detailed view, partly exploded, of a proximal part of the device of FIG. 1 during initial activation, FIG. 4 is a cross-sectional view of the device of FIG. 3, FIGS. 5-6 are detailed, partly exploded, views of an activation mechanism.

Figure 7:
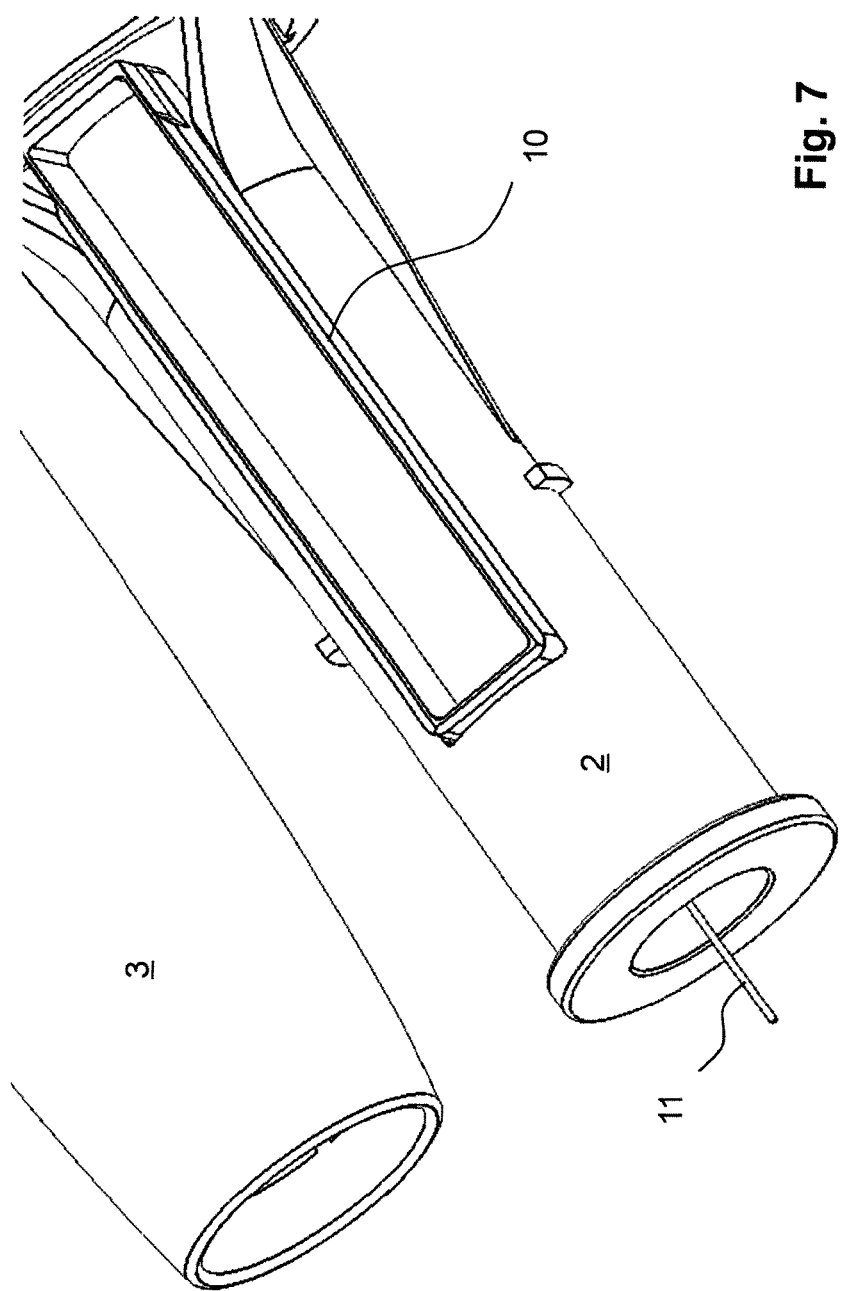
Figure 8:
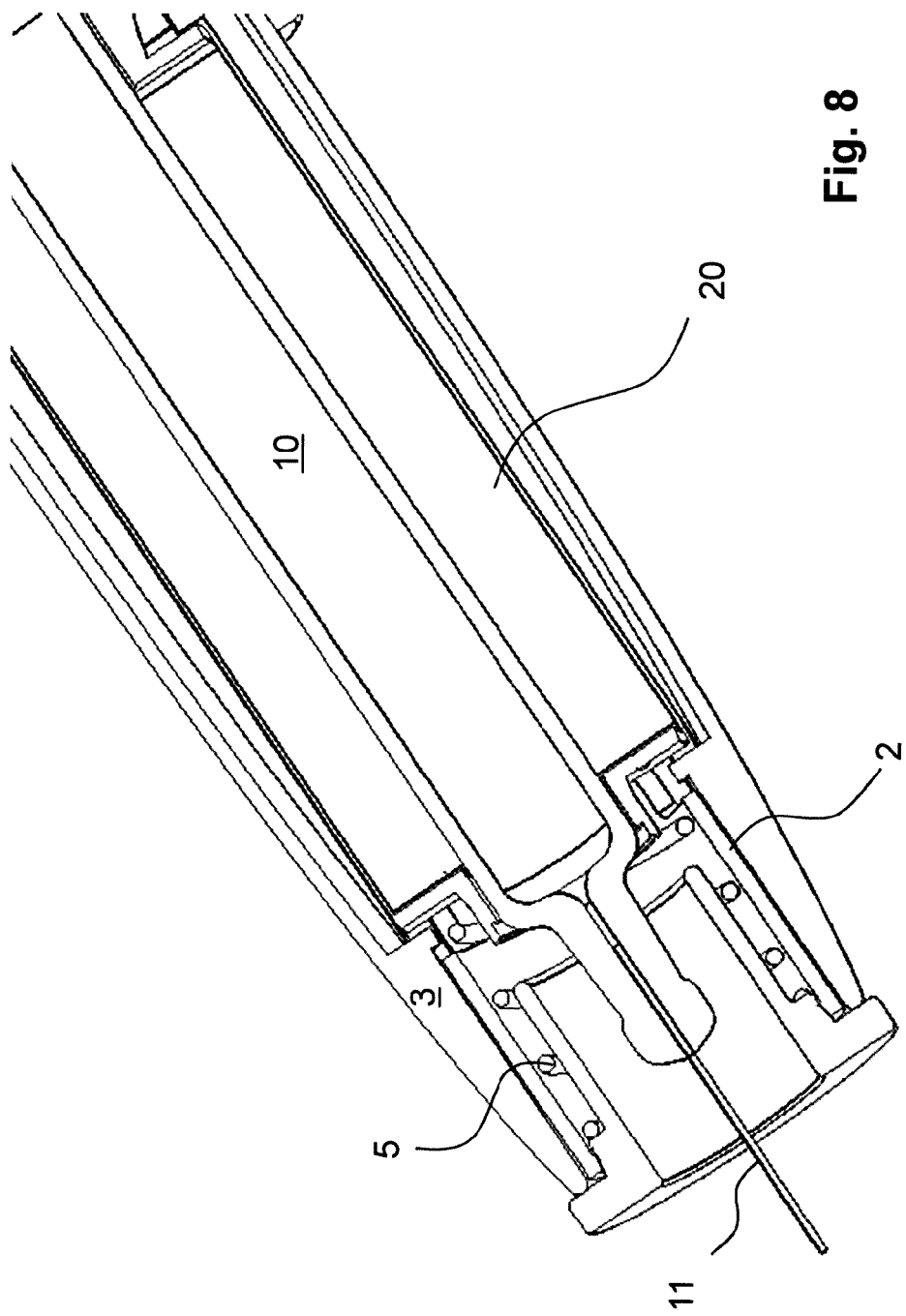
Figure 9:
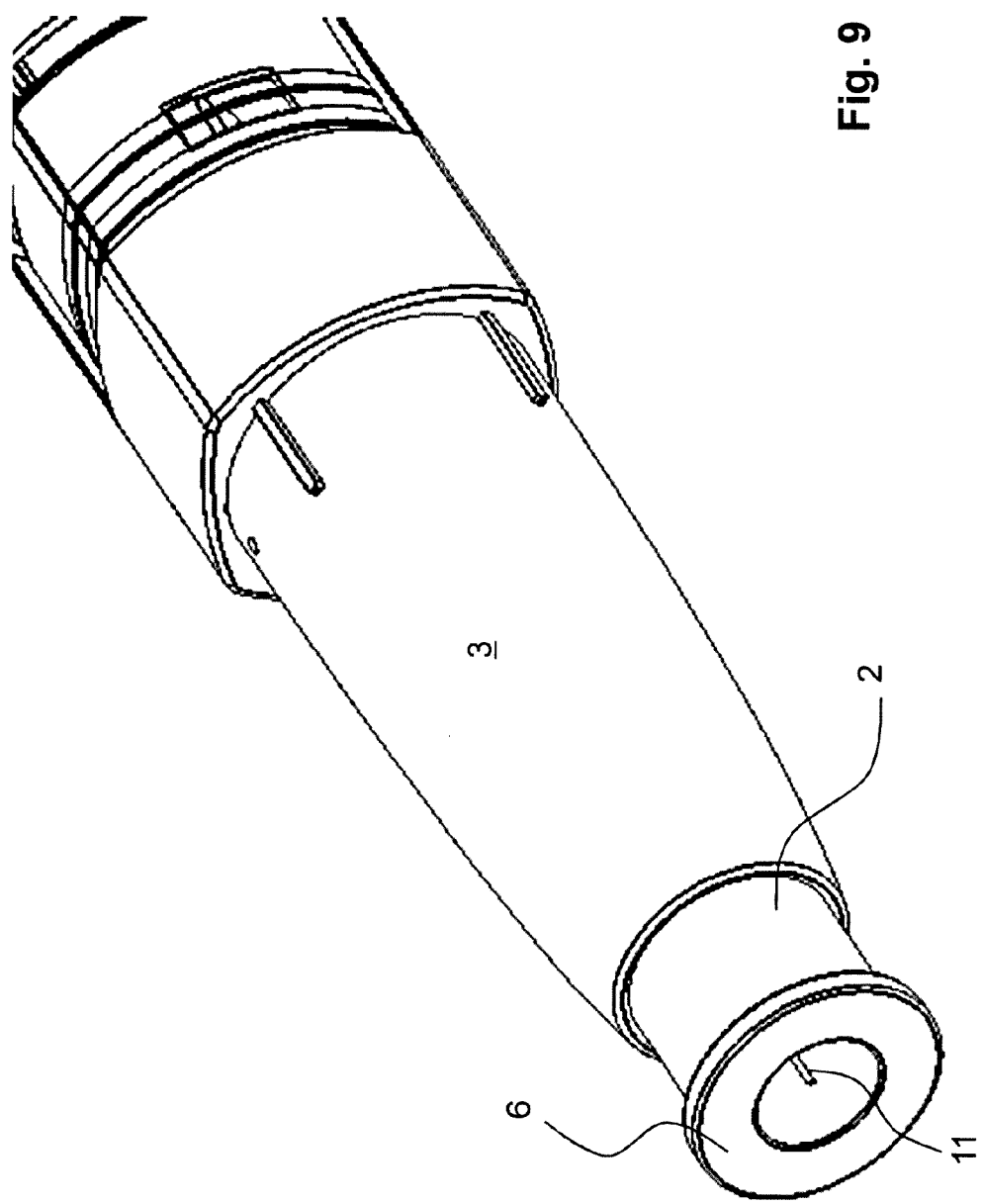
Figure 10:
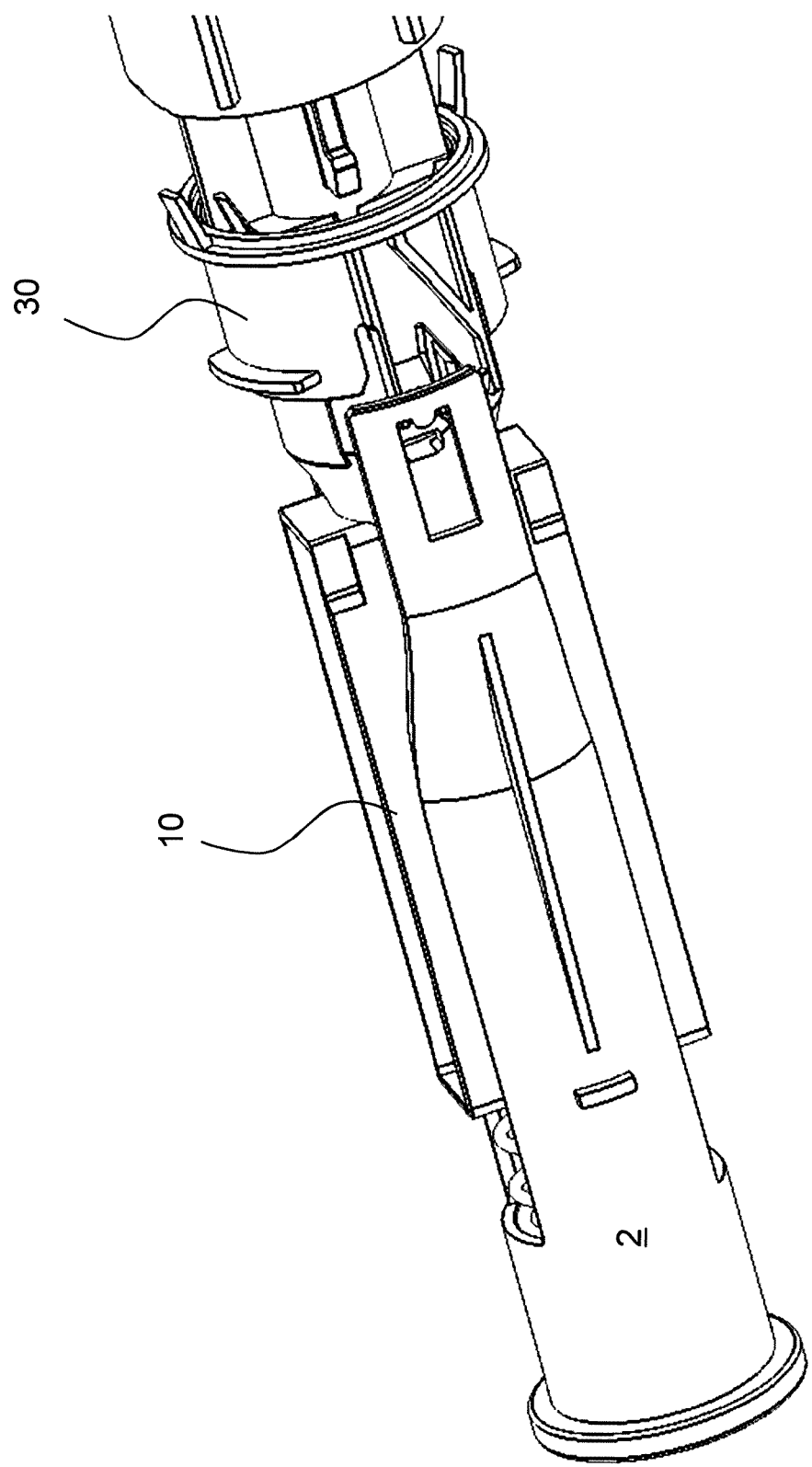

FIG. 7 is a detailed view, partly exploded, of a proximal part of the device of FIG. 1 during penetration/injection, FIG. 8 is a cross-sectional view of the device of FIG. 7, and FIGS. 9, 10 are views after completed injection and withdrawal from injection site.

DETAILED DESCRIPTION OF THE INVENTION

With regard to fastening, mounting, attaching or connecting components of the present invention, unless specifically described as otherwise, conventional mechanical fasteners and methods may be used. Other appropriate fastening or attachment methods include adhesives, welding and soldering. Generally, unless otherwise indicated, the materials for making embodiments of the invention and/or components thereof may be selected from appropriate materials such as metal, metallic alloys, ceramics, plastics, etc.

FIG. 1 shows an injection device having a longitudinal axis L and which is embodied as an auto-injector. The injection device comprises a housing 1 which is formed from a proximal housing part 3 and a distal housing part 4. The proximal housing part 3 is axially fixed to the distal housing part 4 and cannot be easily disassembled by the user. Configuring the injection device in two parts has the advantage that easier assembly of the various components is possible during manufacturing of the device. FIG. 2 shows the injection device further comprising a container holder 20 which accommodates a medicament container 10. The medicament container comprises a container vessel normally made of glass and having an injection needle 11 at the proximal end and a distal movable stopper/piston 12 at the distal end of the container vessel. The container holder 20 is arranged within the housing such that it is longitudinally movable relative to the housing towards the proximal end of the device from a non-delivery position into a delivery position. The medicament container can typically be arranged with or without a flange at its distal end. The medicament container may also comprise a Rigid Needle Shield (RNS) or a Flexible Needle Shield (FNS). Thus, the container holder can be configured to receive a medicament container having either an RNS or an FNS and to hold the medicament container by the flange, by the front part or to hold it by both the flange and the front part. These configurations are well known in the art.

The injection device further comprises a drive mechanism, arranged in the distal housing part. The drive mechanism can be configured to achieve an auto-penetration and auto-injection by using at least one spring. By using two springs, a penetration spring is used for forcing the container holder towards the proximal end of the device and thereby achieving an auto-penetration of the needle. An injection spring is used for forcing a plunger rod towards the proximal end of the device to thereby achieve an auto-injection i.e. an auto delivery of medicament through the needle. Alternatively a single spring may be used to control both the auto-penetration and the auto-injection. Moreover, the drive mechanism is normally configured to hold the spring or springs in a pre-tensioned state. These kinds of drive mechanisms are well known in the art. In this respect it is to be understood that a number of different drive mechanisms can be incorporated in the present invention. The drive mechanism can be of the type disclosed in WO2002047746A1 and in the Swedish patent application SE1150788-6. To the extent not inconsistent with this disclosure, the disclosures of WO2002047746A1 and of the Swedish patent application 1150788-6 are incorporated herein by reference.

The proximal housing part 3 carries an activating member which is embodied as a needle protecting sleeve 2 such that said needle protecting sleeve 2 can be shifted along the longitudinal axis L of the injection device. At a proximal end of the needle protecting sleeve a contact member 6 is attached. The needle protecting sleeve and the contact member are integrally formed. The injection device is shown in FIGS. 1 and 2 with the needle protecting sleeve 2 situated in its initial position. In the initial position, the needle protecting sleeve 2 protrudes beyond the proximal end of the proximal housing part 3. As shown in FIG. 2, the needle protecting sleeve 2 protrudes a distance "d" from the proximal end of the proximal housing. The proximal end of an injection needle 11 which is surrounded by the housing 1 is situated distally with respect to the proximal end of the needle protecting sleeve 2 and, as shown in this case, also distally with respect to the proximal end of the proximal housing part 3. Thus, even when the needle protecting sleeve 2 is shifted in the distal direction by the distance "d", as seen in FIGS. 3 and 4, the proximal end of the injection needle 11 does not protrude beyond the proximal end of the proximal housing part 3. In the activating position of the needle protecting sleeve 2, the tip of the injection needle is protected against being inadvertently accessed.

The needle protecting sleeve 2 is designed to be placed onto an injection site. When the injection device is subsequently pressed against the injection site, the needle protecting sleeve 2 is shifted in the distal direction relative to the device or shifted from the initial to the activating position, which movement of the needle protecting sleeve in the distal direction activates the device.

The proximal end of a needle protecting sleeve spring 5 is supported on a distally directed, circumferential, ledge 7 on the contact member 6 of the needle protecting sleeve 2. The distal end of the needle protecting sleeve spring 5 is supported on a proximally directed collar 21 formed on the container holder 20. Thus, when the needle protecting sleeve 2 is moved into its activating position, the needle protecting sleeve spring 5 is biased by a first amount, FIGS. 3 and 4. Since, the needle protecting sleeve 2 is moved in the distal direction the distance "d", the needle protecting sleeve spring 5 is biased by an amount which is dependent on the distance "d". The resulting spring force may be determined using Hooke's Law.

As mentioned above, movement of the needle protecting sleeve or movement of the needle protecting sleeve with any intermediate member in the distal direction activates the device. According to one embodiment shown in e.g. FIGS. 5 and 6, the distal end of the needle protecting sleeve 2 is arranged with distally directed arms 30, which arms are arranged with radially inwardly extending protrusions 32. These protrusions are arranged to cooperate with a number of ledges 34 on an outer surface of a generally tubular member 36, hereafter named rotator. The rotator which is a part or a component of the drive mechanism is connected to the housing such that the rotator is rotatable but prevented to be axially movable in relation to the to the housing. Initially, when the needle protecting sleeve is in its most proximal, initial, position, the protrusion 32 is positioned at location II in relation to the rotator, FIG. 5. When the needle protecting sleeve 2 is moved in the distal direction relative to the device and to the rotator, the protrusion 32 moves along the ledges 34. The needle protecting sleeve is rotationally locked to the housing by a guiding mechanism. Since one of the ledges 34 in contact with the protrusion is inclined with respect to the longitudinal axis L, the rotator 36 is forced to turn. When the needle protecting sleeve 2 subsequently enters its most distal, activating, position, wherein a proximal end surface 38 of the proximal housing part 3 abuts a distally directed ledge portion 40 of the contact member 6, FIGS. 3 and 4, the protrusion 32 is in position VI in relation to the rotator, FIG. 5. When the rotator has turned a certain amount, penetration and injection triggering means (not shown) which are also part of the drive mechanism are activated.

The injection device may be triggered in different manners known in the art e.g. by only displacing the needle protecting sleeve towards the distal end in relation to the housing, e.g. the mere turning of the rotator causes the trigger, or by first displacing the needle protecting sleeve towards the distal end in relation to the housing and then operating a trigger member or by first operating a trigger member and then displacing the needle protecting sleeve towards the distal end in relation to the housing.

When the injection device is activated, the auto-penetration and consecutively the auto-injection are started i.e. a part or a component of the drive mechanism connected to the container holder together with the medicament container move towards the proximal end from a non-delivery position to a delivery position in relation to the needle protecting sleeve and in relation to the rotator until a shoulder 21 of the container holder abuts an edge 22 of the needle protecting sleeve 2, FIG. 3. Said part or component of the drive mechanism connected to the container holder is the locked to the rotator such that the container holder is prevented to be retracted. In an alternative embodiment, the shoulder 21 may abut an edge of the inner surface of the proximal housing part to avoid a kick back which may otherwise occur when the container holder collides with the distally directed edge 22 of the spring-biased needle protecting sleeve. The medicament is subsequently delivered through the needle 11. As discussed above, different manners to achieve the auto-penetration and auto-injection are known in the art. E.g. the auto-penetration and auto-injection are achieved either through a drive mechanism where only a force from one spring is transferred to move the container together with the container holder and to inject the medicament, or through a drive mechanism where a force from a first spring is transferred to move the container together with the container holder and a force from a second spring is transferred to inject the medicament.

Since the container holder together with the medicament container is displaced in the proximal direction a distance "I" after the injection device has been triggered, FIG. 3, the needle protecting sleeve spring 5 is strained by a second amount which is dependent on the distance "I", in addition to the first amount which is dependent on the distance "d". This increases the spring force of the needle protecting sleeve spring 5.

During the displacement of the container holder together with the medicament container in the proximal direction, the needle protrudes proximally beyond the proximal end of the needle protecting sleeve 2 as seen in FIGS. 7 and 8.

After the medicament has been delivered, the injection device is removed from the injection site and the needle protecting sleeve 2 is displaced in the proximal direction from its activating position to its end position, FIG. 9, due to the needle protecting sleeve spring 5 which is biased by the first distance "d" and the second distance "I", by a force which is greater than the force which was required to shift the needle protecting sleeve 2 by the distance "d" from the initial position. Thus, the needle protecting sleeve 2 can be shifted in the proximal direction by a distance which is larger than the distance "d" by which the needle protecting sleeve 2 was displaced in the distal direction. The needle protecting sleeve 2 is displaced far enough in the proximal direction to its end position wherein its proximal end protrudes proximally beyond the tip of the needle 11, FIG. 9. When the needle protecting sleeve 2 is in the end position where its proximal end protrudes proximally beyond the tip of the needle, the protrusion 32 has travelled in the proximal direction along the ledges 34 of the rotator 36 to a position X in relation to the rotator, FIG. 5. During this travel, the protrusion 32 has passed over a wedge-shaped stop member 42, FIG. 5, which stop member 42 prevents any subsequent movement of the needle protecting sleeve in the distal direction i.e. from the end position to the activation position. It is of course to be understood that other types of locking members may be utilized whereby a locking member of the needle protecting sleeve 2 engages a corresponding locking member of the injection device. In this position i.e. the needle protecting sleeve 2 is in its end position. The needle protecting sleeve 2 is then prevented against moving in the distal direction.

It is to be understood that the embodiments described above and shown in the drawings only are to be regarded as non-limiting examples of the invention and that it may be modified in many ways within the scope of the patent claims.

The invention claimed is:

1. An injection device having distal and proximal ends, comprising:
    a housing;
    a needle-protecting sleeve that is longitudinally movable relative to the housing;
    a container holder that is longitudinally movable relative to the housing toward the proximal end from a non-delivery position to a delivery position; and
    a needle-protecting sleeve spring that is operatively coupled between a distally directed surface of the needle-protecting sleeve and a proximal surface of the container holder such that the needle-protecting sleeve is longitudinally movable toward the distal end of the injection device from an initial position to an activating position and toward the proximal end of the injection device from the activating position to an end position;
    wherein the needle-protecting sleeve spring is strained by a first amount when the needle-protecting sleeve is moved from the initial position to the activating position, and by a second amount when the container holder is moved from the non-delivery position to the delivery position; and the needle-protecting sleeve has a distally directed abutment edge that abuts the proximal surface of the container holder to define the delivery position.

2. The injection device of claim 1, wherein the second amount is larger than the first amount.

3. The injection device of claim 1, wherein the needle-protecting sleeve in the end position is longitudinally immovable relative to the housing.

4. The injection device of claim 1, further comprising a medicament container having a needle and a stopper/piston and being arranged in the container holder.

5. The injection device of claim 4, further comprising a drive mechanism configured to move the container holder and medicament container longitudinally relative to the housing toward the proximal end of the device from the non-delivery position to the delivery position when the needle-protecting sleeve is in the activating position, such that in the delivery position, the needle protrudes beyond the proximal end of the injection device.

6. The injection device according to claim 5, wherein the drive mechanism comprises at least one spring configured to move the container holder and medicament container toward the proximal end of the device and to expel medicament, straining the needle-protecting sleeve spring by the second amount.

7. The injection device of claim 6, wherein the drive mechanism is configured to hold the at least one spring in a pre-tensioned state.

8. The injection device of claim 1, wherein the needle-protecting sleeve in the initial position protrudes proximally beyond a proximal end of the housing by a predetermined distance.

9. The injection device of claim 8, wherein the needle-protecting sleeve in the end position is longitudinally immovable relative to the housing.

10. The injection device of claim 8, further comprising a medicament container having a needle and a stopper/piston and being arranged in the container holder.

11. The injection device of claim 10, further comprising a drive mechanism configured to move the container holder and medicament container longitudinally relative to the housing toward the proximal end of the device from the non-delivery position to the delivery position when the needle-protecting sleeve is in the activating position, such that in the delivery position, the needle protrudes beyond the proximal end of the injection device.

12. The injection device according to claim 11, wherein the drive mechanism comprises at least one spring configured to move the container holder and medicament container toward the proximal end of the device and to expel medicament, straining the needle-protecting sleeve spring by the second amount.

13. The injection device of claim 12, wherein the drive mechanism is configured to hold the at least one spring in a pre-tensioned state.

14. The injection device of claim 8, wherein the needle-protecting sleeve in the end position protrudes proximally beyond the proximal end of the housing by a larger distance than the predetermined distance.

15. The injection device of claim 14, wherein the needle-protecting sleeve in the end position is longitudinally immovable relative to the housing.

16. The injection device of claim 15, further comprising a medicament container having a needle and a stopper/piston and being arranged in the container holder.

17. The injection device of claim 14, further comprising a medicament container having a needle and a stopper/piston and being arranged in the container holder.

18. The injection device of claim 17, further comprising a drive mechanism configured to move the container holder and medicament container longitudinally relative to the housing toward the proximal end of the device from the non-delivery position to the delivery position when the needle-protecting sleeve is in the activating position, such that in the delivery position, the needle protrudes beyond the proximal end of the injection device.

19. The injection device according to claim 18, wherein the drive mechanism comprises at least one spring configured to move the container holder and medicament container toward the proximal end of the device and to expel medicament, straining the needle-protecting sleeve spring by the second amount.

20. The injection device of claim 19, wherein the drive mechanism is configured to hold the at least one spring in a pre-tensioned state.

* * * * *